United States Patent
Christ et al.

(10) Patent No.: US 9,757,205 B2
(45) Date of Patent: Sep. 12, 2017

(54) WEIGHT MODULE FOR A STAND BASE FOR A SURGICAL MICROSCOPE

(71) Applicant: Carl Zeiss Meditec AG, Jena (DE)

(72) Inventors: Hanna Christ, Heidenheim (DE); Frank Koenig, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/489,426

(22) Filed: Apr. 17, 2017

(65) Prior Publication Data
US 2017/0215982 A1    Aug. 3, 2017

Related U.S. Application Data

(60) Division of application No. 14/502,595, filed on Sep. 30, 2014, now Pat. No. 9,622,830, which is a
(Continued)

(30) Foreign Application Priority Data

Mar. 30, 2012   (DE) ................. 10 2012 006 409

(51) Int. Cl.
*G02B 21/24* (2006.01)
*A61B 90/20* (2016.01)
(Continued)

(52) U.S. Cl.
CPC ............ *A61B 90/20* (2016.02); *F16M 11/20* (2013.01); *G02B 7/001* (2013.01);
(Continued)

(58) Field of Classification Search
CPC ... A61B 90/20; A61B 90/50; A61B 2090/504; A61B 2090/5025; G02B 7/001; G02B 21/24; G02B 21/0012; F16M 11/20
(Continued)

(56) References Cited

U.S. PATENT DOCUMENTS

| 3,415,475 A | 12/1968 | Goodman |
| 6,113,054 A | 9/2000 | Ma |

(Continued)

FOREIGN PATENT DOCUMENTS

| DE | 202015003248 U1 * | 10/2015 | ......... E04H 12/2238 |
| JP | 9-323273 A | 12/1997 | |

(Continued)

OTHER PUBLICATIONS

International Search Report dated Nov. 20, 2013 of international application PCT/EP2013/000765 on which this application is based.
(Continued)

*Primary Examiner* — Eret McNichols
(74) *Attorney, Agent, or Firm* — Walter Ottesen, P.A.

(57) ABSTRACT

The stand base is for a surgical microscope. The stand base is for setting up on a floor configured as a planar surface and includes at least a first weight module; a base body defining an underside and accommodating the first weight module; a support arrangement connected to the base body and supporting the stand base with at least three support points in contact engagement with the floor to permit setting up the stand base; the support points conjointly defining a support plane whereat the support points are in contact engagement with the floor; the underside of the base body facing toward the support plane; an ancillary body; the base body having a receiving arrangement in the underside for releasably accommodating the ancillary body; and, the underside of the base body and the support plane conjointly defining a smallest spacing therebetween which is greater than 10 cm.

4 Claims, 4 Drawing Sheets

Related U.S. Application Data continuation of application No. PCT/EP2013/000765, filed on Mar. 14, 2013.

(51) Int. Cl.
  *G02B 7/00* (2006.01)
  *G02B 21/00* (2006.01)
  *F16M 11/20* (2006.01)
  *E04H 12/22* (2006.01)
  *A61B 90/50* (2016.01)
  *F16M 11/42* (2006.01)

(52) U.S. Cl.
  CPC ......... *G02B 21/0012* (2013.01); *G02B 21/24* (2013.01); *A61B 90/50* (2016.02); *A61B 2090/504* (2016.02); *A61B 2090/5025* (2016.02); *E04H 12/2238* (2013.01); *F16M 11/42* (2013.01)

(58) Field of Classification Search
  USPC ........................................ 248/127, 129, 519
  See application file for complete search history.

(56) References Cited

U.S. PATENT DOCUMENTS

| | | |
|---|---|---|
| 6,305,659 B1 | 10/2001 | Metelski |
| 6,405,990 B2 | 6/2002 | Davis et al. |
| 6,446,930 B1 | 9/2002 | Li |
| 6,833,950 B2 | 12/2004 | Schmidt |
| 6,869,058 B2 * | 3/2005 | Tung ................... E04H 12/2238 248/519 |
| 6,938,871 B1 * | 9/2005 | Carlson ................... G09F 17/00 248/519 |
| 7,213,869 B1 | 5/2007 | McClellan |
| 7,896,299 B2 | 3/2011 | Chinuki et al. |
| 9,464,452 B2 * | 10/2016 | Higgs ................... E01F 13/022 |
| 2001/0040208 A1 | 11/2001 | Li |
| 2002/0179788 A1 | 12/2002 | Crookham et al. |
| 2004/0262866 A1 | 12/2004 | Kraus |
| 2005/0017148 A1 | 1/2005 | Tung |
| 2005/0199774 A1 | 9/2005 | Reese |
| 2005/0205727 A1 | 9/2005 | Nerger |
| 2008/0237412 A1 | 10/2008 | Chinuki et al. |
| 2009/0159762 A1 | 6/2009 | Chinuki et al. |
| 2015/0267860 A1 | 9/2015 | Schutz et al. |

FOREIGN PATENT DOCUMENTS

| | | | |
|---|---|---|---|
| WO | 91/03194 A1 | 3/1991 | |
| WO | 98/53244 A1 | 11/1998 | |
| WO | WO 2016005321 A1 * | 1/2016 | ......... E04H 12/2238 |

OTHER PUBLICATIONS

International Preliminary Report on Patentability and Written Opinion dated Oct. 9, 2014 of international application PCT/EP2013/000765 on which this application is based.

Translation and German Office action of the German Patent Office dated Feb. 6, 2013 of corresponding German patent application 10 2012 006 409.8.

* cited by examiner

WEIGHT MODULE FOR A STAND BASE FOR A SURGICAL MICROSCOPE

CROSS REFERENCE TO RELATED APPLICATIONS

This application is a divisional application of U.S. patent application Ser. No. 14/502,595, filed Sep. 30, 2014, which, in turn, is a continuation application of international patent application PCT/EP2013/000765, filed Mar. 14, 2013, designating the United States and claiming priority from German application 10 2012 006 409.8, filed Mar. 30, 2012, and the entire content of the above applications is incorporated herein by reference.

BACKGROUND OF THE INVENTION

Surgical microscope systems often comprise a surgical microscope, a retaining system to which the surgical microscope is fastened, and a stand base, which forms the base of this retaining system. Since surgical microscopes are available in various levels of equipment, the weight of the surgical microscope changes depending on the level of equipment. A weight change of the surgical microscope has effects on the retaining system and the stand base of the retaining system. In order to avoid a tilting of the stand base in any case, this is therefore to be formed so as to be as heavy as possible. An increase of the weight of the surgical microscope on the one hand may therefore be associated on the other hand with a necessary increase of the weight for the stand base.

A microscope stand with a multi-part foot with weights which can be mounted in a cavity or on an initially open cavity in the stand base body without rotating the stand base body is known from U.S. Pat. No. 6,305,659.

Carl Zeiss Meditec AG, under the name "S5", offers a stand base on which the invention is based. This stand base includes a hollow stand base main body, which can be equipped from the underside with weights. These weights are secured by retaining elements in the stand base main body.

Although on the one hand a high stability is necessary, which is achieved by a high weight of the stand base, there is on the other hand also the desire, however, to design the surgical microscope system in such a way that it can be moved between different locations. For this reason, it is also known to equip the stand base with castors in order to enable a change in position of the entire surgical microscope system by moving the stand base on the castors. However, an unnecessary increase of the weight of the stand base significantly impairs the ability to move the surgical microscope system to another location. It is therefore usual in practice to equip the stand base with the minimum weight necessary in order to ensure on the one hand a secure footing of the surgical microscope system and on the other hand to enable maximum movement comfort when moving the system on the castors of the stand base.

In order to accommodate the wide range of various equipment variants of a surgical microscope and the associated differences in weight, there is thus a need to be able to equip the associated stand base in a number of different weight levels. Since the weight differences of the various levels of development of a surgical microscope may be considerable, the conventional method of fitting weights in a stand base body may no longer be sufficient to cover the necessary large weight range reliably and cost-effectively.

In addition to the requirement of a stand base with variable weight, there is a demand for the avoidance of the risk of foot injuries. The standard DIN EN 60601-1 3ed is incorporated herein by reference and demands protection in order to prevent injuries to a user's feet. For this purpose, the distance between the underside of the stand base and the floor or ground must be either greater than 12 cm or smaller than 3.5 cm. This safety requirement is referred to as underrun protection.

SUMMARY OF THE INVENTION

It is an object of the invention to provide a stand base for a surgical microscope, in which the total weight of the stand base can be adapted easily and cost-effectively over a wide range and at the same time the safety requirements of the underrun protection can be reliably observed.

The stand base of the invention is for a surgical microscope. The stand base is for setting up on a floor configured as a planar surface and includes at least a first weight module; a base body defining an underside and being configured to accommodate the first weight module; a support arrangement connected to the base body and being configured to support the stand base with at least three support points in contact engagement with the floor to permit setting up the stand base; the support points conjointly defining a support plane whereat the support points are in contact engagement with the floor; the underside of the base body facing toward the support plane; an ancillary body; the base body having a receiving arrangement configured in the underside for releasably accommodating the ancillary body; and, the underside of the base body and the support plane conjointly defining a smallest spacing therebetween which is greater than 10 cm.

The stand base according to the invention for a surgical microscope for positioning on a floor formed as a planar surface has a base body, which is configured in such a way that it can be fitted with at least one first weight module. The base body has a base body underside and a supporting device, which is connected to the base body and which is, or can be, brought into contact with the floor at least at three points for positioning the stand base, wherein the base body underside faces the plane defined by the at least three points. The base body underside also has a receiving arrangement for detachable connection to an ancillary body. Here, the shortest distance between the base body underside and this plane is greater than 10 cm.

In the smallest equipment variant, the stand base can be used without additional weight and without an ancillary body. The shortest distance between the base body underside of the base body and the floor is greater than 10 cm. Due to the large distance, it is therefore impossible for the instep of a foot to become wedged, thus resulting in high user friendliness. With the next-highest level of development of a mounted surgical microscope, the weight of the stand base can be adapted by being fitted with one or more weights. Due to the complete integration of the weight modules in the base body, the distance between the base body and the floor is reliably maintained in this case too. Because of the receiving device on the base body underside, an ancillary body can be attached quickly and easily to the base body in order to achieve a further increase in weight.

The stand base according to the invention for a surgical microscope is designed for example such that the receiving device for the ancillary body is formed as a planar surface. The formation of the receiving device as a planar surface can be produced easily and cost-effectively. The receiving device therefore has the smallest surface possible. This facilitates necessary hygiene measures. A necessary complementary surface of an ancillary body attached to the receiving device can be produced just as easily.

The receiving device of the stand base according to the invention for a surgical microscope may have one or more threaded bores. These can be used to detachably fasten the ancillary body to the receiving device. In particular, two, three or four threaded bores can be provided. Two, three or four threads can be formed in the receiving device cost-effectively. The ancillary body can be attached to the base body quickly and cost-effectively by means of fastening, for example by two screws.

The base body may have a cavity that is open toward the base body underside for the detachable introduction of the at least one first weight module. The introduction of a weight module into a cavity that is open on the underside of the base body has the advantage that the weight module is not visible from the side and from above. The stand base can therefore be provided with additional weight in a manner invisible to the user.

For example, the cavity in the base body can be cylindrical, in particular cuboidal or circular cylindrical. A rectangular, oval or round cross section of the cavity as viewed from the base body underside are advantageous. Such a comparatively simple geometric shape of the cavity can be produced cost-effectively. The height of the cavity is to be produced cost-effectively at a constant height. A corresponding weight module of complementary shape can also be produced easily. This is preferably introduced into the cavity with a form fit from the base body underside.

In accordance with the invention, the stand base according to the invention may be detachably connected at the base body underside thereof to the ancillary body by means of the receiving device. This equipment variant of the stand base has the advantage of being able to easily add or remove weight to/from the stand base. A base body model can thus be adapted for different levels of equipment of surgical microscopes and for the associated different weight of the surgical microscopes in the various levels of equipment.

With the stand base according to the invention for a surgical microscope, to which an ancillary body is attached at the receiving device, the greatest distance between the ancillary body underside, which faces the above-specified plane defined by the at least three points, and this plane is, for example, less than 4 cm, preferably less than 3.5 cm. If the greatest distance between the underside of the ancillary body and the floor has a distance of less than 4 cm, the foot of the user can only push against the ancillary body as far as the toes or the toe region of a shoe. A wedging of the ball region is therefore reliably precluded. In order to securely and reliably meet the requirements for the underrun protection, the distance is to be formed advantageously so as to be less than 3.5 cm.

A hollow space for detachably introducing a weight module can be formed in the ancillary body. If the ancillary body also has a hollow space into which one or more weight modules can be introduced and can be fastened, there is even greater play when adapting the weight of the stand base balancing the weight of the surgical microscope.

The stand base according to the invention for a surgical microscope, to which an ancillary body is attached at the receiving device, can be formed such that the cavity in the base body and the hollow space in the ancillary body have the same cross section as viewed from the underside.

This is a very important advantage with the combination of the base body and an attached ancillary body. It is thus possible to introduce one, two, three or more weight modules into the stand base from below without having to previously remove the ancillary body. The range of the weight adaptation is thus very large.

The stand base according to the invention for a surgical microscope, to which an ancillary body is attached at the receiving device, is preferably designed in such a way that the ancillary body is adapted in a form-fitting manner and/or in terms of the geometric shaping or physical shaping (design) to the base body. In the case of a form-fitting configuration, there are minimal joins between the ancillary body and base body. This facilitates the cleaning of the stand base considerably, and additionally has advantages for the necessary hygiene measures with use of the surgical microscope system in an operating theater. With a configuration of adapted design and with a surface structure of the ancillary body that is adapted, in particular identical, to the base body, the stand base as a whole is advantageously provided with an attractive visual appearance. The base body and ancillary body are perceived as a uniform overall body and also portray such a body in terms of hygienic requirements.

The stand base according to the invention for a surgical microscope can also be formed such that the shortest distance between the base body underside and the plane is greater than 12 cm.

If this distance between the underside of the base body or the underside of the lower installed weight module and the floor has a value of greater than 12 cm, the protection of a foot of the user can be achieved reliably. The foot of the user can be moved beneath the stand base as far as the instep without any risk of the forefoot or the toes becoming wedged.

The stand base according to the invention for a surgical microscope can also be formed such that the greatest distance between the base body underside and the plane is less than 20 cm.

If the greatest distance between the base body underside is less than 20 cm, there is sufficient stability for the stand base with reliably attainable protection of the foot of the user. If the distance is greater than 10 cm and less than 20 cm, the plane beneath the stand base, for example the floor of an operating theater, can be easily reached by a cleaning system and kept clean.

A weight module for a stand base according to the invention for a surgical microscope has an upper side and an underside. A first through-hole is provided between the upper side and underside, wherein a first threaded bore is formed in the underside parallel to the first through-hole. A middle axis parallel to the bore central axis is located over the line of connection between the first bore central axis of the through-hole and the first thread central axis of the threaded bore, such that the distance between the first bore central axis and the middle axis has the same value as the distance between the middle axis and the first thread central axis. Here, the first thread is formed in such a way that the outer diameter of the first threaded bore is smaller than the diameter of the first through-hole.

This construction has the advantage that, with use of two identical weight modules, wherein the second weight module is rotated about the middle axis by 180° relative to the first weight module, the through-hole of one weight module is aligned with the thread of the other weight module. A screw connection between the two weight modules can thus be produced very easily.

The above-described weight module for a stand base according to the invention for a surgical microscope may have a second through-hole, which is formed parallel to the first through-hole, and a second threaded bore, which is formed parallel to the second through-hole. The second threaded bore is formed in such a way that the outer diameter of the second threaded bore is smaller than the diameter of the second through-hole. The distance between the second bore central axis of the second through-hole to the middle axis has the same value as the distance between the second thread central axis of the second threaded bore to the middle axis. Here, the first bore central axis and the first thread central axis form a first plane and the second bore central axis and the second thread central axis form a second plane, wherein this first and this second plane are identical or are orthogonal to one another, wherein the middle axis lies on both planes.

The formation of two through-holes and two threaded bores in a weight module has the advantage that, with use of two structurally identical weight modules, wherein the second weight module is rotated about the middle axis through 180° with respect to the first weight module, the two through-holes of one weight module are aligned with the two threaded bores of the other weight module. Due to the connection of the two weight modules using two screws, these are interconnected in a manner secured against rotation.

The weight module for a stand base according to the invention for a surgical microscope may have an underside formed so as to have a shape complementary to the upper side thereof. When assembling two weight modules formed in this way, the upper side of the first weight module can be brought against the underside of the second weight module in a form-fitting manner. A possibility of connection between two weight modules without gaps is thus provided very easily. If the surfaces are formed in a surface form deviating from the planar surface, it may be sufficient to connect the two weight modules in a manner secured against rotation using just one screw.

In accordance with the invention, a system having two identical weight modules, specifically a first weight module and a second weight module, is provided for a stand base according to the invention, in which the second weight module is rotated about the middle axis through 180° relative to the first weight module, such that the first bore central axis of the first through-hole in the second weight module and the first thread central axis of the first threaded bore in the first weight module lie on a first straight line and the second bore central axis of the second through-hole of the second weight module and the second thread central axis of the second threaded bore of the first weight module lie on a second straight line.

With this connection technique, as many weight modules as desired can be interconnected when each weight module is rotated through 180° relative to the adjacent weight module. At the same time, cost advantages are provided by the possibility of using single, identical weight modules.

With the stand base according to the invention for a surgical microscope, it is possible to cover a large variable weight range and at the same time to reliably satisfy the safety requirements of underrun protection.

In the smallest equipment variant, the stand base can be used without additional weight and without ancillary body. The distance between the underside of the stand base body and the floor may be greater than 12 cm. The safety requirements for underrun protection are thus satisfied with high user friendliness. It is not possible for a foot instep to become wedged. With the next-highest level of development of the mounted surgical microscope, the weight of the stand base can be adapted by fitting one or more weights. Due to the complete integration of the weight modules in a cavity in the stand base body, the distance between the stand base body and the floor can be reliably maintained in this case also.

With a further necessary increase of the weight of the stand base, an ancillary body can be attached on the underside of the base body. By attaching the ancillary body to the underside of the base body, a new distance is given between the underside of the ancillary body and the floor. In this case, the distance may be less than 3.5 cm and would therefore satisfy a further safety requirement of underrun protection in a reliable and user-friendly manner.

Since the ancillary body in turn contains a hollow space for at least one weight module, a further margin for the adaptation of the weight of the stand base is advantageously provided. The cavity in the base body and the hollow space in the ancillary body is advantageously formed such that identical weight modules can be introduced into both bodies and secured. Following attachment of the ancillary body, a new cavity is thus formed by the combination of the cavity and the hollow space in the base body and the ancillary body, respectively. A weight module can therefore be introduced into the base body advantageously from beneath through the ancillary body. Due to the possibility of using identical weight modules both for the base body and the ancillary body, cost advantages are provided with the production of the weight modules.

Due to the large number of different possibilities for introducing weight modules into the base body and fastening an ancillary body to the underside of the base body, into which weight modules can in turn be introduced, a very large variable weight range is provided. A variable equipping of the stand base that is as simple as possible can thus be achieved when uniformly staggered weight values are selected. If the weight of the ancillary body is selected here such that it is twice or three times or another multiple of a weight module, the weight increase can also be implemented with an ancillary body attached to the base body in a uniform gradation. Handling and time advantages are thus provided for the user. There is no need for any complicated processing operations. The desired weight increase can be established very quickly.

A weight increase of the stand base is to be versatile. The weight of the weight module is expediently defined in a unit that is as small as possible. This gives the advantage of producing lighter weight modules. If more than just one weight can be installed in the main body, different weight increases of the base body can already be achieved, even without additional bodies.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
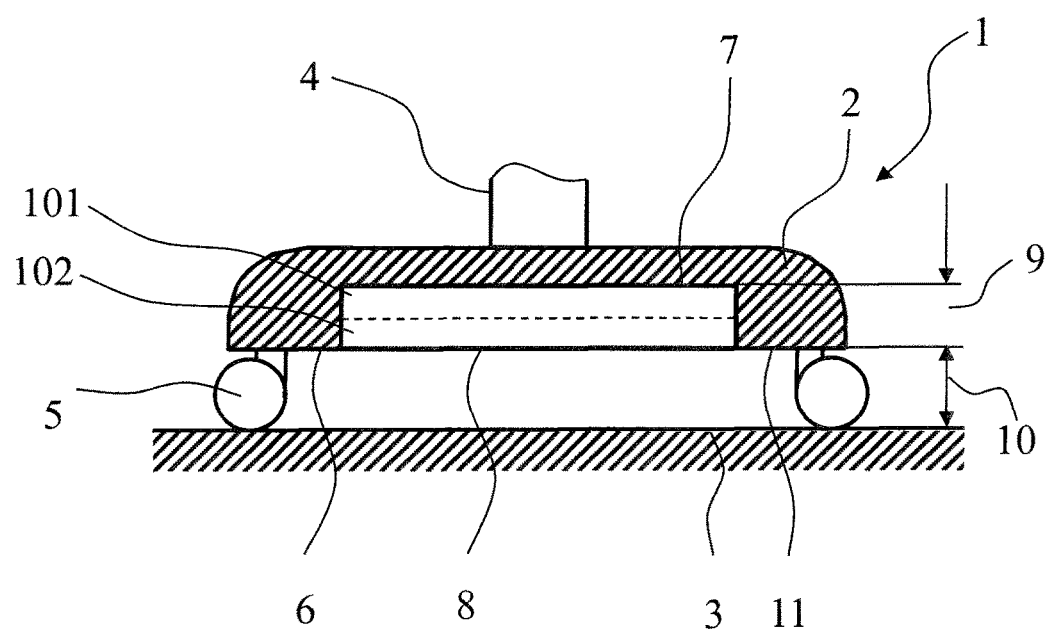
FIG. 1 is a side elevation view, in section, of a first embodiment of the stand base of the invention.

FIG. 1 is a side elevation view, in section, showing a first embodiment of a stand base 1. The core of the stand base 1 forms a base body 2. The base body 2 can be configured in any form. For example, a cylindrical, cuboidal, star-shaped or "H"-shaped design as viewed from above is conceivable. A stand post 4 is attached to the upper side of the base body 2, and a retaining device (not shown here) for a surgical microscope is fastened to the stand post. The underside 6 of the base body 2 is substantially parallel to a floor 3. The floor 3 constitutes a substantially planar surface, on which the stand base 1 can be positioned or on which the stand base 1 can be moved. The underside 6 has a receiving device 11. The receiving device 11 enables the attachment of an ancillary body (not shown here). The receiving device 11 may additionally have bores, threads or recesses (not shown here), for example a milled groove.

The stand base 1 can be equipped on the underside 6 thereof with three to five, preferably four, support elements. The support elements serve to position the stand base on the floor 3. The support elements are formed in the embodiment shown as castors 5. The castors 5 allow a movement of the stand base on the floor 3. The castors 5 can be equipped with a clamping or fixing device (not shown) in order to reliably prevent an unintentional displacement of the stand base 1.

The stand base body 2 has a cavity 7, which is open on the underside 6 of the stand base. The cavity 7 is cuboidal as viewed from the underside 6, but may also be square, round or configured in any other form. The form of the cavity 7 is defined substantially by a base surface 8 and a height 9. A distance 10 between the underside 6 of the stand base to the floor 3 is 12 cm in this embodiment in order to meet the provisions, currently in force, of the standard "DIN EN 60601-1 3ed" for avoiding foot injuries, referred to as underrun protection.

A weight can be introduced into and secured in the cavity 7 in the base body 2. The weight may comprise a single weight module 101 or may be composed of two weight modules (101, 102). The weight modules (101, 102) are preferably identical. The weight modules (101, 102) are each configured such that they are slightly smaller than the cavity 7 and can therefore be easily introduced thereinto and fastened therein.

Figure 3:
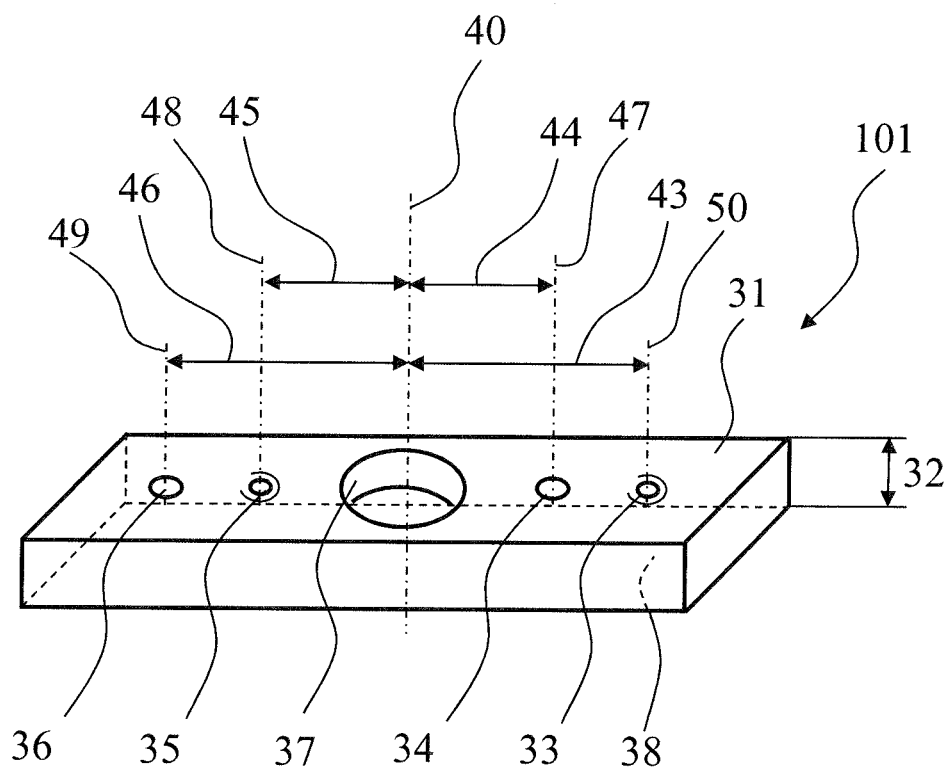
FIG. 3 is a perspective view of an embodiment of a weight module.

FIG. 3 shows an embodiment of a weight module 101. The weight module 101 is cuboidal. It thus has a rectangular underside 31 and a height 32. The base surface of the underside 31 of the weight module is smaller than the base surface 8 of the cavity 7 so that the weight module 101 can be easily introduced into the cavity 7. In FIG. 1, the height 9 of the cavity 7 is illustrated to be twice as large as the height 32 of the weight module 101.

When introducing the two weight modules (101, 102) together into the cavity 7, the lower weight module 102 may terminate flush with the underside 6 of the base body 2. The lower weight module 102 may also be fastened deeper in the cavity 7, such that a distance is provided between the base surface 8 of the underside 31 of the lower weight module 102 and the floor 3 that is greater than the distance 10 between the underside 6 of the base body 2 and the floor 3. However, it is also possible that the lower weight module 102 cannot be introduced completely into the cavity 7 and thus protrudes. In this case, the distance between the underside of the lower weight module 102 and the floor 3 is smaller than the distance 10. However, it must be ensured that the distance between the underside of the lower weight module 102 and the floor 3 meets the conditions for the underrun protection and is thus at least 12 cm.

When fitting the base body 2 from FIG. 1 with weights, there are thus three variants. There may be no weight module 101 at all introduced into the cavity 7, there may be a single weight module 101 introduced into the cavity 7, or there may be two weight modules 101 and 102 fastened together in the cavity 7. If the individual weight of a weight module is for example 10 kg, the weight of the base body 2 can thus be increased by 10 kg or by 20 kg in this example. In any case, it is ensured that the distance 10 between the underside 6 of the base body 2 and the floor 3 is not changed.

The weight modules 101 and 102 can be fastened in the cavity 7 by screwing, riveting, adhesive bonding or any other fastening methods. The weight modules 101 and 102 can be permanently fastened or attached by a releasable connection in the cavity 7.

It is also conceivable to install a damping device, for example a foil, thin foam, thin felt or another suitable material, between the weight modules 101 and 102 or to install such a device between the weight module 101 and the base body 2 in order to achieve a vibration and acoustic damping of the weight modules 101 and 102. It must be ensured that the distance between the underside of the lower weight module 102 and the floor 3 is greater than 12 cm as a result of the installation of the weight modules 101 and 102, inclusive of the interposed damping materials, so as to thus meet the conditions for the underrun protection. The total height, composed from the two values of the height 32 of the weight modules 101 and 102 and the material thickness of the additional damping material, is preferably smaller on the whole than the height 9 of the cavity 7, such that the underside of the lower weight module 2 terminates flush with the underside 6 of the base body 2 or is introduced completely into the cavity 7.

It is also possible for at least three weight modules to be introduced into the cavity 7 of the base body 2, such that the total height of all weight modules together is smaller than or equal to the height 9 of the cavity 7.

Figure 2:
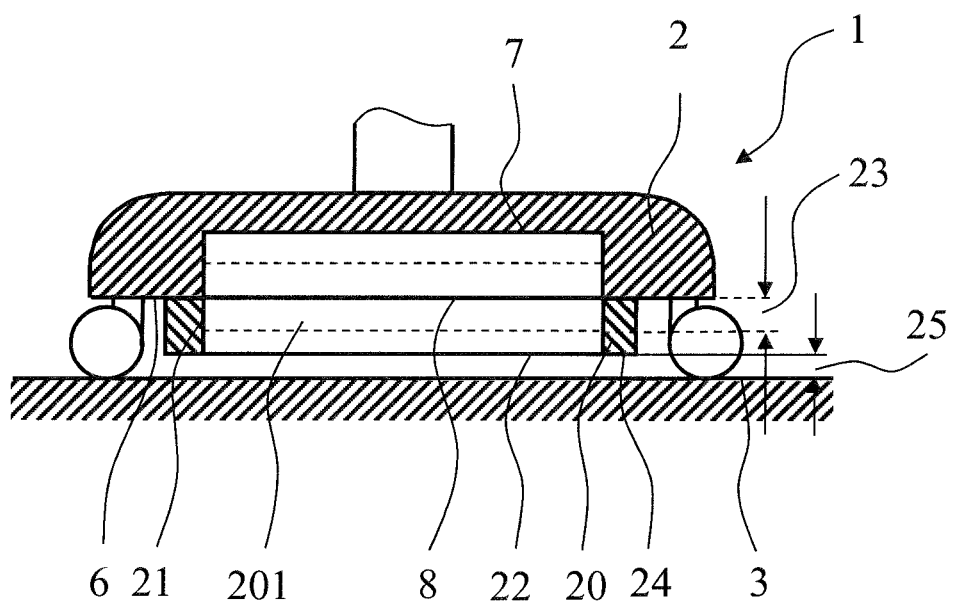
FIG. 2 is a side elevation view, in section, of a second embodiment of the stand base according to the invention with an attached ancillary body.

FIG. 2 is a side elevation view, in section, of a second embodiment of the stand base 1 of the invention with an attached ancillary body 20.

FIG. 2 shows the inventive stand base 1 from FIG. 1. The ancillary body 20 is attached to the receiving device 11 on the underside 6 of the base body 2. The ancillary body 20 can be fastened to the receiving device 11 of the base body 2 by screwing, adhesive bonding, riveting or another known fastening method. The ancillary body 20 can be permanently fastened or can be attached to the base body 2 by a releasable connection. However, the ancillary body 20 is preferably fastened to the underside of the base body 2 with threaded fasteners.

Due to the attachment of the ancillary body 20, the distance 25 between the underside 24 of the ancillary body 20 and the floor 3 is changed such that the provisions of standard "DIN EN 60601-1 3ed" for avoiding foot injuries (underrun protection) are satisfied. In this exemplary embodiment, the distance 25 is less than 3.5 cm.

The ancillary body 20 is advantageously formed such that it is adapted in terms of pattern (surface structure) and in terms of geometric shaping (design) to the base body 2. For example, if the base body 2 is formed in such a way that it has an H-shape in plan view, the ancillary body 20 may also demonstrate an H-shape in plan view. It is also conceivable for the base body 2 to be formed in such a way that it has a star shape, an X-shape, an O-shape, a U-shape or a Z-shape. In this case, the ancillary body 20, adapted to the base body 2, may also be formed in a star shape, X-shape, O-shape, U-shape or Z-shape. The number of stand base arms may be even, for example four stand base arms in the case of the H-shape or X-shape. The number of stand base arms may also be odd, for example three or five stand base arms in the case of the star shape. The ancillary body 20 may have a closed and smooth outer surface. The ancillary body 20 may have the same color and/or surface structure as the base body 2.

The ancillary body 20 has a hollow space 21. This hollow space 21 can be formed in such a way that it has a base surface 22 and forms an upwardly and downwardly open hollow space 21. An individual weight module 201 can be easily introduced into and fastened in this hollow space 21. The weight module 201 is preferably structurally identical to the weight module 101 and the weight module 102.

It is also possible for the hollow space 21 to be formed in such a way that two or three weight elements, which have the same size and shape of a weight module 201, can be introduced jointly and fully into the hollow space 21.

The weight module 201 can be fastened in the hollow space 21 by screwing, riveting, adhesive bonding or another known fastening method. The weight module 201 can be permanently fastened or can be attached in the hollow space 21 by a releasable connection.

The base surface 22 of the hollow space 21 of the ancillary body 20 has the same shape and size as the base surface 8 of the cavity 7 of the base body 2. Following attachment of the ancillary body 20 to the receiving device 11, a common cavity is thus produced by the combination of the cavity 7 of the base body 2 and the hollow space 21 of the ancillary body 20.

When fitting the base body 2 from FIG. 2 with weights, four variants are thus provided. Firstly, there may be no weight module 101 at all introduced into the cavity 7. Secondly, there may be a single weight module 101 introduced into the cavity 7. Thirdly, there may be two weight modules 101 and 102 fastened together in the cavity 7. Fourthly, there may be a total of three weight modules 101, 102 and 201 introduced into the common cavity, which is composed of the cavity 7 and the hollow space 21.

If the individual weight of a weight module (101, 102, 201) is for example 10 kg, the weight of the base body 2, to which the ancillary body 20 is attached, can be increased in this embodiment according to FIG. 2 by 10 kg, 20 kg or 30 kg.

On the whole, there is thus a further margin for the adaptation of the weight of the stand base 1. For this example, it is assumed that the individual weight of the ancillary body 20 is 30 kg. In order to load the base body 2 without ancillary body 20 with 10 kg or 20 kg, it is sufficient to introduce and to fasten a weight module 101 or two weight modules (101, 102) in the cavity 7. With a desired weight loading of the base body 2 by 30 kg, by contrast merely the ancillary body 20 is attached to the base body 2. In order to achieve a further increase of the weight of the base body 2 by 40 kg, 50 kg or 60 kg, the ancillary body 20 is fastened to the base body 2 and a weight module 101 or two weight modules (101, 102) or three weight modules (101, 102, 201) is/are additionally introduced into and fastened in the cavity, comprising the cavity 7 and hollow space 21. These specified weights are to be considered exemplary, and a wide range of weight values for the ancillary body 20 and the weight modules (101, 102, 201) are conceivable.

FIG. 3 shows an embodiment of the weight module 101. All weight modules (101, 102, 201) are preferably of identical size. The weight module 101 is cuboidal and has an upper side 38, the underside 31 and the height 32. A first thread 35 and a second thread 33 are formed in the underside 31. The weight module 101 further has a first through-hole 34, a second through-hole 36 and an opening 37. The threads (33, 35) can be formed as blind bore threads or can be formed continuously, such that the length of the thread (33, 35) corresponds to the height 32. The thread 33 and the thread 35 preferably have the same thread diameter. The through-hole 34 and the through-hole 36 are greater in diameter than the thread diameter of the threads (33, 35). The through-hole 34 and the through-hole 36 preferably have the same diameter. Both through-holes 34 and 36 have a countersink or bore (not shown here) on the upper side 38 in order to fully receive a screw head.

A thread central axis 48 of the first thread 35 is arranged at a distance 45 from a middle axis 40. A bore central axis 47 of the first through-hole 34 is at a distance 44 from the middle axis 40. The distance 44 and the distance 45 are of equal size. A thread central axis 50 of the second thread 33 has a distance 43 from the middle axis 40. A bore central axis 49 of the second through-hole 36 is at a distance 46 from the middle axis 40. The distance 43 and the distance 46 are of equal size.

In this embodiment, the weight module 101 has an opening 37. This opening 37 makes it possible to guide a component, for example a screw, or an assembly tool, for example an Inbus key, through the weight module 101. The opening 37 is preferably located in the center of the weight module 101, such that these openings 37 are arranged one above the other with an assembly of a number of weight modules (101, 102, 201), such that a component or a tool can be easily guided through all weight modules (101, 102, 201).

Figure 4:
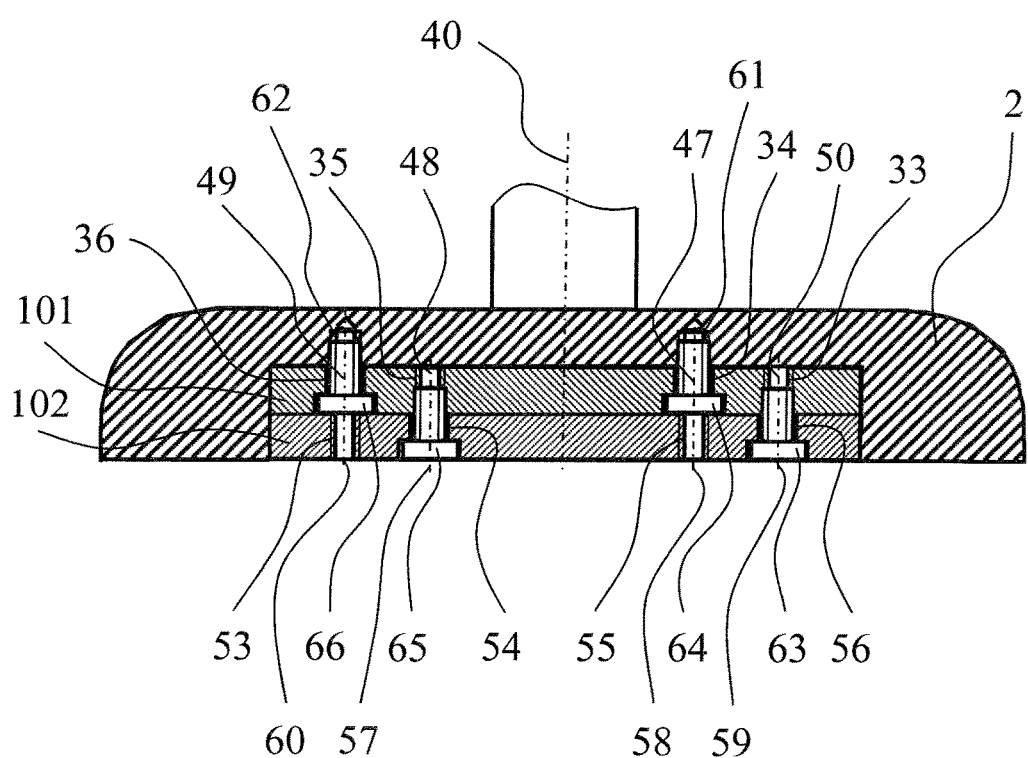
FIG. 4 is a side elevation view, in section, showing two weight modules connected.

FIG. 4 is a side elevation view, in section, showing a connection of the two weight modules 101 and 102.

The weight module 101 is screwed by means of a screw 64, which is introduced into the first through-hole 34, with a thread 61 in the base body 2. The weight module 101 is additionally screwed by means of a screw 66, which is introduced into the second through-hole 36, with a thread 62 in the base body 2.

The weight module 102 is installed in a manner rotated about the axis of symmetry 40 through 180° with respect to the weight module 101. The first through-hole 54 of the weight module 102 is thus arranged opposite the first thread 35 of the weight module 101. The thread central axis 48 of the first weight module 101 is aligned with the diameter central axis 57 of the second weight module 102. In addition, the second through-hole 56 of the weight module 102 is arranged opposite the second thread 33 of the weight module 101, and the thread central axis 50 of the first weight module 101 is aligned with the diameter central axis 59 of the second weight module 102.

The screw 63, which is introduced into the second through-hole 56 and is screwed into the second thread 33, thus connects the weight module 101 to the weight module 102. The screw 65, which is screwed into the first through-hole 54 and is screwed into the first thread 35, also connects the weight module 101 to the weight module 102.

Three or more weight modules (101, 102, 201) can also be interconnected in this way.

It is understood that the foregoing description is that of the preferred embodiments of the invention and that various changes and modifications may be made thereto without departing from the spirit and scope of the invention as defined in the appended claims.

LIST OF REFERENCE NUMERALS 1 stand base
2 base body
3 floor 4 stand post
5 castors
6 underside of the base body 2
7 cavity in the base body 2
8 base surface of the cavity in the base body 2
9 height of the cavity 7 in the base body 2
10 distance of the underside 6 of the stand base from the floor 3
11 receiving device
20 ancillary body
21 hollow space in the ancillary body 20
22 base surface of the hollow space 21 in the ancillary body 20
23 height of the hollow space 21 in the ancillary body 20
24 underside of the ancillary body 20
25 distance of the underside 24 of the ancillary body 20 from the floor 3
31 base surface of the first weight module 101
32 height of the first weight module 101
33 second thread in the first weight module 101
34 first through-hole in the first weight module 101
35 first thread in the first weight module 101
36 second through-hole in the first weight module 101
37 opening in the first weight module 101
38 upper side of the first weight module 101
40 middle axis
43 distance between axis of symmetry 40 and second thread 33
44 distance between axis of symmetry 40 and the first through-hole 34
45 distance between axis of symmetry 40 and first thread 35
46 distance between axis of symmetry 40 and the second through-hole 36
47 bore central axis of the first through-hole 34
48 thread central axis of the first thread 35
49 bore central axis of the second through-hole 36
50 thread central axis of the second thread 33
53 second thread in the second weight module 102
54 first through-hole in the second weight module 102
55 first thread in the second weight module 102
56 second through-hole in the second weight module 102
57 bore central axis of the first through-hole 54
48 thread central axis of the first thread 55
49 bore central axis of the second through-hole 56
50 thread central axis of the second thread 53
61 first thread in the base body 2
62 second thread in the base body 2
63 first screw
64 second screw
65 third screw
66 fourth screw
101 first weight module
102 second weight module
201 third weight module

What is claimed is:

1. A weight module for a stand base for a surgical microscope, the stand base being for setting up on a floor configured as a planar surface and the stand base including: a base body defining an underside and being configured to accommodate the weight module; a support arrangement connected to the base body and being configured to support the stand base with at least three support points in contact engagement with the floor to permit setting up the stand base; the support points conjointly defining a support plane whereat the support points are in contact engagement with the floor; the underside of the base body facing toward the support plane; an ancillary body; the base body having a receiving arrangement configured in the underside for releasably accommodating the ancillary body; and, the underside of the base body and the support plane conjointly defining a smallest spacing therebetween which is greater than 10 cm; the weight module comprising:
a weight module body having an upper side and an underside;
said weight module body defining a first through-hole between said upper side and said underside;
said weight module body further having a first threaded bore in said underside;
said first threaded bore extending parallel to said first through-hole;
said first through-hole defining a first through-hole central axis and a first through-hole diameter;
said first threaded bore defining a first threaded bore central axis;
said first threaded bore central axis and said first through-hole central axis defining an imaginary connecting line therebetween;
said weight module body further having a middle axis disposed on said imaginary connecting line such that a first distance between said first through-hole central axis and said middle axis has the same value as a second distance between said middle axis and said first threaded bore central axis; and,
said first threaded bore is configured such that said first threaded bore has an outer diameter which is smaller than said first through-hole diameter.

2. The weight module of claim 1, wherein:
said weight module body further defines a second through-hole between said upper side and said underside;
said second through-hole has a second through-hole diameter and extends parallel to said first through-hole;
said weight module body further having a second threaded bore has a second threaded bore outer diameter and extends parallel to said second through-hole;
said second threaded bore outer diameter is smaller than said second through-hole diameter;
said second through-hole defines a second through-hole central axis;
said second threaded bore defines a second threaded bore central axis;
said second through-hole central axis having a third distance to said middle axis;
said second threaded bore central axis having a fourth distance to said middle axis;
said third distance being equal to said fourth distance;
said first through-hole central axis and said first threaded bore central axis defining a first plane;
said second through-hole central axis and said second threaded bore central axis defining a second plane;
said first plane and said second plane being identical or orthogonal to each other; and,
said middle axis lies in both said first and said second plane.

3. The weight module of claim 1, wherein said upper side and said underside of said weight module body are configured complementary in form to each other.

4. A system comprising:
a first weight module and a second weight module;
a stand base for a surgical microscope, the stand base being for setting up on a floor configured as a planar surface and the stand base including: a base body defining an underside and being configured to accommodate said first and second weight modules; a support arrangement connected to the base body and being configured to support the stand base with at least three support points in contact engagement with the floor to permit setting up the stand base; the support points conjointly defining a support plane whereat the support points are in contact engagement with the floor; the underside of the base body facing toward the support plane; an ancillary body; the base body having a receiving arrangement configured in the underside for releasably accommodating the ancillary body; and, the underside of the base body and the support plane conjointly defining a smallest spacing therebetween which is greater than 10 cm;

said first weight module and said second weight module each including a respective weight module body having a module upper side and a module underside;

each of said weight module bodies defining a first through-hole between the corresponding ones of said module upper side and said module underside;

each of said weight module bodies further having a first threaded bore in the corresponding one of said module undersides;

each of said first threaded bores extending parallel to the corresponding one of said first through-holes;

each of said first through-holes defining a respective first through-hole central axis and a respective first through-hole diameter;

each of said first threaded bores defining a respective first threaded bore central axis;

respective ones of said first threaded bore central axes and said first through-hole central axes each defining a respective imaginary connecting line therebetween;

said weight module bodies of said first and said second weight modules conjointly defining a middle axis disposed on each of said imaginary connecting lines such that a respective first distance between each of said first through-hole central axes and said middle axis has the same value as a second distance between said middle axis and the corresponding one of said first threaded bore central axes; and, each of said first threaded bores being configured such that each of said first threaded bores has a respective outer diameter which is smaller than the corresponding one of said first through-hole diameters;

each of said weight module bodies further defining a second through-hole between the corresponding ones of said upper side and said module underside;

each of said second through-holes having a respective second through-hole diameter and extending parallel to the corresponding one of said first through-holes;

each of said weight module bodies further having a respective second threaded bore having a respective second threaded bore outer diameter and extending parallel to the corresponding one of said second through-holes;

each of said second threaded bore outer diameters being smaller than the corresponding one of said second through-hole diameters;

each of said second through-holes defining a respective second through-hole central axis;

each of said second threaded bores defining a respective second threaded bore central axis;

each of said second through-hole central axes having a respective third distance to said middle axis;

each of said second threaded bore central axes having a respective fourth distance to said middle axis;

each of said third distances being equal to the corresponding one of said fourth distances; and, said second weight module being arranged rotated 180° about said middle axis relative to said first weight module such that said first through-hole central axis of said second weight module and said first threaded bore central axis of said first weight module lie on a first imaginary straight line and said second through-hole central axis of said second weight module and said second threaded bore central axis of said first weight module lie on a second imaginary straight line.

* * * * *